United States Patent [19]

Conrad et al.

[11] Patent Number: 4,496,245
[45] Date of Patent: Jan. 29, 1985

[54] LIQUID CHROMATOGRAPHY PROPORTIONING VALVE AND MIXER

[75] Inventors: Frederick L. Conrad, Poughkeepsie, N.Y.; Louis R. Palmer, Newtown; Arthur A. Roberts, Danbury, both of Conn.

[73] Assignee: International Business Machines Corp., Armonk, N.Y.

[21] Appl. No.: 472,903

[22] Filed: Mar. 7, 1983

[51] Int. Cl.³ .................. B01F 7/16; B01F 13/08; B01F 15/02
[52] U.S. Cl. .................. 366/143; 366/160; 366/179; 366/182; 366/273
[58] Field of Search ........... 366/143, 160, 177, 179, 366/182, 273, 274; 137/606, 624.18, 624.11

[56] References Cited

U.S. PATENT DOCUMENTS

| | | | |
|---|---|---|---|
| 1,519,798 | 12/1924 | Pilkington et al. | 366/274 |
| 2,495,895 | 1/1950 | Hervert | 366/273 |
| 2,793,166 | 5/1957 | Hatch | 366/143 |
| 2,912,343 | 11/1959 | Collins et al. | 366/273 |
| 2,999,673 | 9/1961 | Kessler | 366/273 |
| 3,941,517 | 3/1976 | Miyahara | 366/273 |
| 4,162,689 | 7/1976 | Zdrodowski | 137/624.12 |

FOREIGN PATENT DOCUMENTS 1150850  5/1969  United Kingdom ............... 137/606

Primary Examiner—Philip R. Coe
Attorney, Agent, or Firm—Douglas R. McKechnie

[57] ABSTRACT

A combined proportioning valve and mixer usable in a liquid chromatography system for mixing solvents in predetermined ratios, includes a magnetically driven stirrer rotatably disposed in a central chamber. Plural inlet lines allow solvents to enter the chamber at spaced positions. The chamber also communicates with outlet lines and is provided with means for preventing air bubbles from being entrapped in the stirrer and blocking flow through the system. Selectively controlled valve members control the flow of solvents through the inlet lines so as to achieve the preselected ratio of solvent mixing.

11 Claims, 2 Drawing Figures

LIQUID CHROMATOGRAPHY PROPORTIONING VALVE AND MIXER

FIELD OF THE INVENTION

This invention relates to improvements in combined proportioning valves and mixers usable in a liquid chromatography (LC) system to mix solvents in predetermined ratios.

BACKGROUND OF THE INVENTION

In commercially available liquid chromatography systems, it is common place to provide a plurality of solvent sources which allows the user to select which solvent or solvents will be used in a particular analytical run or experiment, and to select two or more solvents which are mixed together in desired proportions that are either fixed for a period of time or vary over a period of time, the latter operation being known as gradient programming. The trend in chromatography is towards systems providing higher and higher degrees of resolution and to accomplish this, it is necessary that when two or more solvents are used in an experiment, the solvents be mixed as thoroughly as possible. Poor or improper mixing leads to erratic and irreproducible results.

In general, the systems of the prior art allow each solvent reservoir to be connected through a selectively controllable valve whereby operation of the series of valves controls which solvent is being used and the desired proportion of plural solvents. Commonly, the valves are actuated by a solenoid which is controlled through some form of a solvent gradient or program control system. In one commercially available valve, three solenoid actuators are mounted at right angles to each other upon a valve body and control three valve members so as to allow solvents from three different reservoirs to be proportional. Mixing occurs in a chamber located downstream of the valve members and the mixing is done without any additional mechanical mixing device. In other words, the mixing occurs due to the flow conditions in the chamber. There are some disadvantages to such a system. First, the passageways are not hydraulically balanced and this causes slightly different flow characteristics and proportioning to occur dependent upon which valves are open. Second, the valve has a common outlet in line with one of the inlets but at right angles to two other inlets causing different solvents to flow under primarily laminar flow conditions in such a manner as to not promote any mixing of the solvents. Third, the valve has dead spaces located in passages downstream of the valve members which accumulate solvents when the valve members are shut. Thus, if only one valve member is open, the desired solvent then washes undesired solvent from the dead spaces of the other solvent passages.

Another problem occurs because of the occasional presence of air, within the system, which might leak in, e.g., due to poor fittings. This problem is particularly troublesome where the valve body is formed of an inert material, such as polytetrafluoroethelene. With such material, air bubbles tend to adhere to the material and it is necessary that the solvent flowing through the system wash or otherwise dislodge the air bubbles from the material and pass it through the system. However, most solvents have a low degree of wettability relative to the material and it therefore becomes difficult to dislodge the air bubbles with the result that sometimes an air blockage might occur to thereby distort proportioning.

SUMMARY OF THE INVENTION

Accordingly, one of the object of the invention is to provide an improved mixing valve for use in an LC system allowing two or more solvents to flow through the system and be thoroughly mixed.

Another object is to provide a combined proportioning valve and mixing device wherein selectively actuated valve members allow the solvents to be introduced in desired portions and mixed with the assistance of a mechanical mixing action that positively promotes thorough mixing.

Another object of the invention is to provide an LC proportioning valve and mixer which enables the user to observe that the mixer is operating.

Still another object is to provide a novel mixing valve chamber which encloses a magnetically driven stirrer, the chamber being so shaped as to prevent air from being entrapped in the stirrer and thereby blocking the flow of solvent through the system.

Still another object is to provide a mixer for plural solvents in which the various flow lines are hydraulically balanced and in which any dead space is minimized.

In general, in accordance with the invention, a proportioning valve and mixer has a central mixing chamber. A plurality of inlet lines open into the chamber and a plurality of outlet lines allow liquid to flow from the chamber. Three solenoid actuated valve members are placed respectively within the inlet lines and in conjunction with the body of the device, form a valve for selectively controlling the flow of solvents. A star wheel magnetically driven stirrer is disposed in the chamber. The chamber is formed with a recess at its upper end which allows air to flow through the mixer without becoming entrapped in the star wheel and thereby blocking flow. The inlet lines are equiangularly spaced around the chamber and are the same size and shape to provide a hydraulic balance. A glass window encloses one end of the chamber and allows the operator to view operation of the stirrer.

Other objects and advantages of the invention will be apparent from the following description taken in connection with the accompanying drawing wherein.

DETAILED DESCRIPTION

Figure 1:
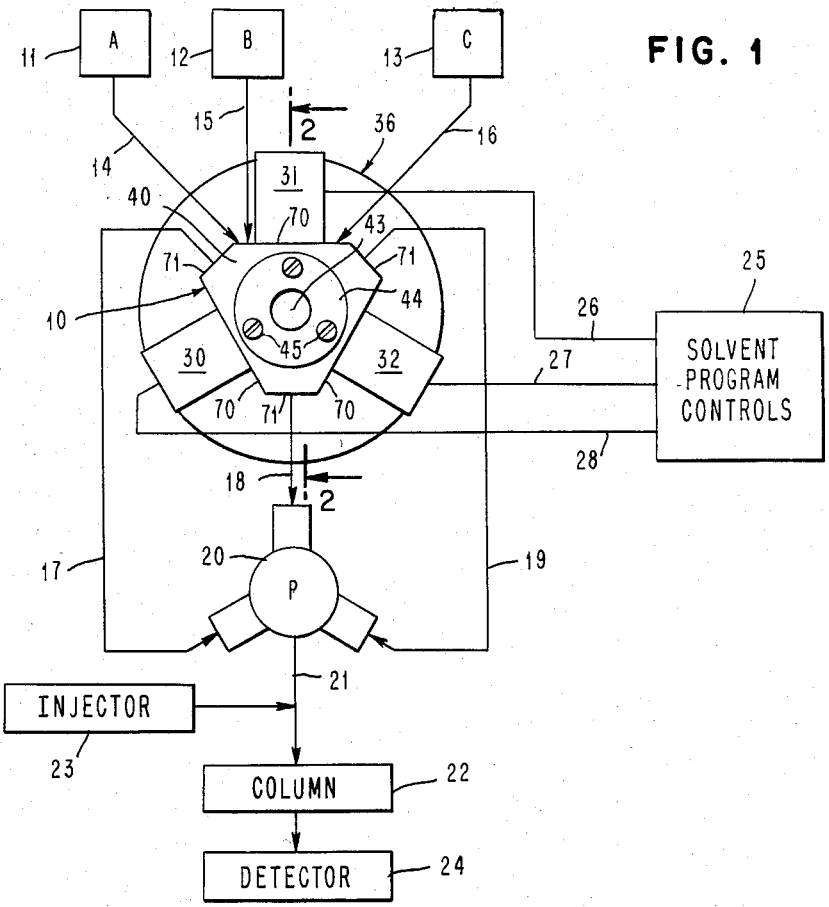
FIG. 1 is a schematic view of an LC system embodying the invention.

Referring now to the drawing, the LC system shown in FIG. 1 comprises a proportioning valve and mixer 10 hereinafter referred to more simply as a "device". Except for the details of device 10, the remaining part of the system is constructed and operated in accordance with the prior art and its operation will be described herein only to the extent of understanding the design and operation of device 10. Three reservoirs 11, 12 and 13 respectively contain solvents A, B and C the specific nature of each being selected by the user to accomplish the desired analysis. The reservoirs are connected by tubes 14, 15 and 16 to the inlets of device 10. The outlets of device 10 are connected by lines 17, 18 and 19 to the inlets of a three headed pump 20. The outlet of pump 20 is connected to line 21 which in turn is connected to an LC column 22. An LC injector 23 serves to allow a sample to be injected into the solvent or solvents flowing through line 21. In operation, as the solvents of sample flow through column 22, the sample is separated into its constituents in accordance with known principles of chromatography and the effluent from column 22 passes through a detector 24. The solvent program controls 25 are connected by leads 26, 27 and 28 to solenoids 30, 31 and 32 of device 10. Controls 25 selectively actuates the solenoids so as to allow any one of the three solvents to flow through device 10 or any combination of the three solvents in either a fixed or variable proportion.

Figure 2:
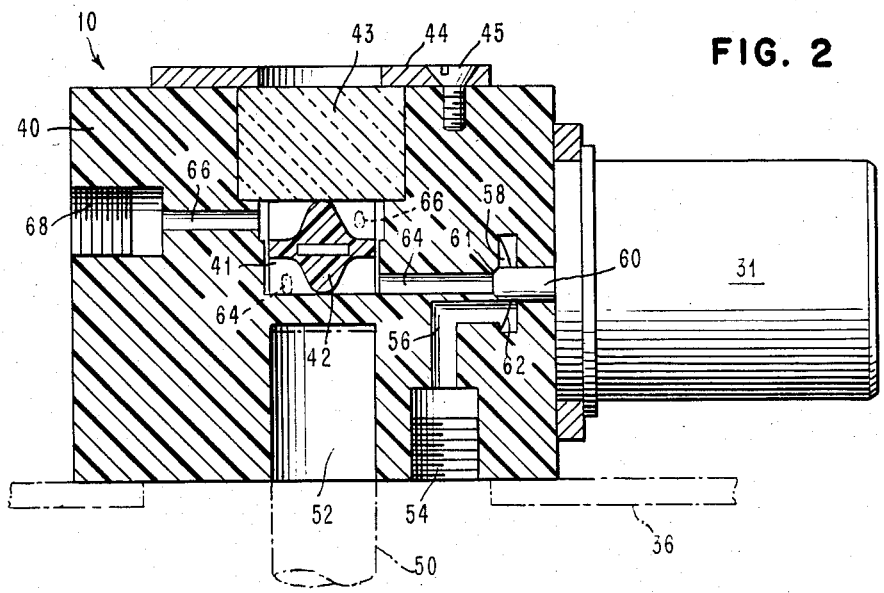
FIG. 2 is an enlarged view, partly in section, viewed generally along reference line 2—2 of FIG. 1. of the proportioning valve and mixer constituting the invention.

Referring to FIG. 2, device 10 comprises a body 40 having a mixing chamber 41 formed therein. A magnetically driven star wheel stirrer 42 is located in chamber 41. A clear glass cylindrical plug 43 overlies chamber 41 and is held in place by a hold-down ring 44 secured by screws 45 to body 40. Device 10 is intended for operation in a horizontal position so that window 43 faces upwardly allowing an operator to observe rotation of stirrer 42. Body 40 is formed from a relatively inert material which is preferrably type 316 stainless steel (non-magnetic), although it is shown as being of plastic. Device 10 is adapted to be mounted on top of a stirrer drive 36 which includes a rotary driving member 50 adapted to be inserted into a cylindrical cavity 52 formed in body 40. Member 50 creates a rotary magnetic field that magnetically couples with stirrer 42 to rotate the stirrer about a vertical axis extending coaxially through chamber 41.

Device 10 has three identical inlets and three identical outlets that are equiangularly spaced from each other. As shown in FIG. 2, each inlet comprises an enlarged threaded portion 54 adapted to be connected to a fitting mounted on one of tubes 14-16. A passageway 56 extends upwardly from portion 54 and then outwardly and opens into a chamber 58 that is somewhat flattened and cylindrical. A valve member 60 extends through chamber 58 and is connected to a flexible diaphragm 62 that seals off one side of the chamber. The left end of valve member 60 coacts with a valve seat 61 formed by body 40 at one end of passageway 64. Passageway 64 extends between chamber 58 and 41. Upon actuation of solenoid 31, valve member 60 moves away from valve seat 61 allowing fluid to flow through the inlet defined by 54, 56, 58 and 64 into mixing chamber 41. Each outlet comprises a passageway 66 extending between chamber 41 and an enlarged threaded portion 68 to be connected to a conventional fitting on one of the outlet lines 17-19.

As best seen in FIG. 2, chamber 41 is cylindrical and includes a lower portion that is of a smaller diameter than that of the upper portion, the purpose of which will be described below. Each of passageways 64 communicates with the lower portions 21 and each of the outlets 66 communicates with the upper portion of chamber 41. Starwheel stirrer 42 is of conventional construction and includes a body of inert material such as polytetrafluoroethylene. A magnet is embedded in the body and coacts with the rotating driving magnetic field to thereby rotate the stirrer. The body includes a central web and a series of spokes at either end. As indicated previously, air bubbles have an affinity for the specific material used and tend to cling or tightly adhere which makes it difficult for the solvents to flush away or break away the air bubbles. If chamber 41 were formed of the same diameter throughout such as the diameter of the lower end, air bubbles tend to accumulate within the spokes of the upper side of stirrer 42 and eventually create an air blockage preventing the flow of fluids through device 10. Thus, the reason for providing the enlarged upper portion is to create a space radially outwardly of stirrer 42 which allows the air bubbles to be discharged through centrifugal action from between the spokes and flow outwardly until they pass through passageways 66. This enlargement at the upper end is a critical feature of the invention.

During operation of device 10, one of solenoids 30-32 will be actuated at all times so that there is some fluid flowing through the device from one of the reservoirs to pump 20, due to the sucking or pumping action of the pump, at all times.

As should be obvious to those persons skilled in the art, the relative size and volume of the mixing chamber and the cyclic operation of the solenoid valves to achieve a desired flow rate, are related. To better understand this relationship, an illustrative example will be given, it being understood that other sizes and dimensions can be used without departing from the scope of the invention. The diameter of the lower portion of chamber 41 is 0.39" and its height is 0.657". The diameter of the upper portion is 0.406" and its length is 0.469". The clearance between stirrer 42 and the lower portion of 41 is 0.010" and the total free volume within the mixing chamber is 0.4 milliliters. The operating cycle for the solenoids has a period of 20 seconds. Over this period, if more than one solvent is to be mixed, the solenoids are individually actuated for a period of time to bring about the desired proportions. For example, assume that solenoid 30 controls the flow of solvent A and that solenoid 31 controls the flow of solvent B, and that it is desired to mix the solvents A to B in a three to one proportion. Thus, solenoid 30, which controls the flow of solvent A, would be then actuated for 15 seconds and solenoid B would be actuated for 5 seconds, this period of cyclic operation being repeated throughout the experimental process. Assume further that the flow rate through the system is 1 milliliter per minute. Thus, during each 20 second cycle, one third of a milliliter or 0.33 milliliters flows. The volume that flows within this period of time is less than the volume of chamber 41, which as indicated above is 0.4 milliliters. Thus, as the solvents during one period or cycle of operation flow into chamber 41, they are mixed therein with solvents that have flowed during prior cycles to effectively and continuously mix the solvents even through the solvents flow from a reservoir only one at a time.

In accordance with another aspect of the invention, the various inlets and outlets are hydraulically balanced. This is accomplished because each of the inlets are identical and are equiangularly spaced about chamber 41. The outlet lines are also identically and similarly equiangularly spaced. All open into the chamber at the same angle and all are of the same size and length so that there is no difference in the flow characteristics through any of them.

Further, the length of each of passages 64 within the inlets is minimized. This minimization comes about in the following manner. Note that the shape of valve body 40 as viewed in FIG. 1, is hexagonal and has three large flat surfaces 70 upon which the solenoids 30-32 are mounted and three smaller flat surfaces 71 through which the outlet lines extend. This allows the solenoids to be mounted at the same distance from the vertical axis of device 20. The mounting flanges of the solenoids limit how inwardly close the solenoids could be placed to each other. Thus, the length of passages 64 is minimized and this creates the advantage of minimizing the problem of dead space and solvent washout. This problem occurs when for example, it is desired to flow only one solvent through the system. At the beginning of such operation, the passages 64 associated with the other solvents are filled with the other solvents which gradually bleed out or are washed out as the desired solvent passes through the device 10. By minimizing the length and volume of passages 64, this problem is also minimized.

It should also be appreciated that the location of the inlets is somewhat a matter of choice. By placing them on the bottom of device 10, the inlet lines can be somewhat hidden within drive 36. However, they could be located beneath the outlet lines and connected by passages 56 which would then have to extend laterally instead of vertically, to enter into chambers 58. Such location is further advantageous in that should any leakage occur due to poor fittings, the leakage occurs above the top of the stirrer, rather than internally above the stirrer motor.

It should be also apparent that other changes can be made in the details and arrangement of parts. While we have illustrated and described the preferred embodiment of the invention, it is understood that we do not limit ourselves to the precise construction herein disclosed and the right is reserved to all changes and modifications coming within the scope of the invention as defined in the appended claims.

Having thus described our invention, what we claim as new and desire to secure by Letters Patent is:

1. In a device for continuously mixing solvents flowing into a liquid chromatography system, the combination of:
    a body having a cylindrical mixing chamber therein, said chamber having a cylindrical first portion of a constant first diameter and a cylindrical second portion of a constant second diameter larger than that of said first diameter, said first and second portions constituting the entire mixing chamber, said body further having inlet passage means communicating with said first portion of said chamber for continuously admitting solvents to be mixed into said chamber, and outlet passage means communicating with said second portion of said chamber for conducting solvents mixed in said chamber away therefrom and into said chromatography system; and
    a magnetic star wheel stirrer rotatably disposed in and substantially filling said chamber, said stirrer being rotatable about an axis of said chamber, said star wheel stirrer extending through said first and second portions and being adapted to be driven by a rotary magnetic field, said star wheel stirrer having a central web and two spoked sections on either side of said web, one spoked section being disposed in said first portion for mixing solvents therein and the other spoked section being disposed in said second portion inwardly of said outlet passage means for mixing solvent in said second portion, said stirrer rotating in a cylindrical volume within said chamber which volume has a diameter slightly less than said first diameter, whereby the larger diameter of said second portion allows any gases in said mixing chamber to flow around said stirrer and outwardly through said outlet passage means without becoming entrapped in said other spoked section and blocking the flow of liquids through said device.

2. The device of claim 1 wherein said device comprises a clear window overlying said mixing chamber and allowing observation of movement of said stirrer.

3. The device of claim 1 comprising:
    selectively operated valve means for controlling the flow of solvents through said inlet passage means.

4. The device of claim 1 wherein said inlet passage means comprises at least two separate passage means each one adapted to admit a different solvent into said mixing chamber.

5. The device of claim 4 comprising:
    at least two selectively operated valve means each operatively associated with a different one of said separate passage means for selectively controlling the flow of solvents through said passage means.

6. The device of claim 5 wherein said valve means are selectively operable over a period of time to proportionately control the flow of solvents over such period, said stirrer being operative to mix said solvents in a preselected proportion in said mixing chamber.

7. The device of claim 4 wherein:
    said separate passage means are hydraulically balanced providing identical flow characteristics.

8. The device of claim 1 comprising:
    said inlet passage means comprising three hydraulically-balanced inlet passages opening into said mixing chamber through three equiangularly spaced ports; and
    three selectively operable valve means operative to selectively control the flow of solvents through respective ones of said inlet passages.

9. The combination of claim 8 wherein:
    each of said valve means comprises a valve member and a solenoid connected to move said valve member for controlling the flow of solvent through one of said inlet passages.

10. The combination of claim 9 wherein:
    said valve body comprises three flat sides equiangularly spaced from each other and surrounding said chamber;
    each of said solenoids being mounted on one of said flat surfaces and spaced equiangularly from the other ones of said solenoids.

11. The combination of claim 10 wherein:
    each of said inlet passages extending radially away from said mixing chamber in line with the axis of one of said solenoids, and having a short length between said mixing chamber and the associated one of said valve members, so as to create a minimal dead volume containing one of said solvents.

* * * * *